United States Patent
Rosen

(10) Patent No.: US 7,090,495 B1
(45) Date of Patent: Aug. 15, 2006

(54) DENTAL IMPLANT SCREW AND POST SYSTEM

(76) Inventor: Dan Rosen, 25029 Rey Alberto Ct., Calabasas, CA (US) 91302

( * ) Notice: Subject to any disclaimer, the term of this patent is extended or adjusted under 35 U.S.C. 154(b) by 0 days.

(21) Appl. No.: 11/180,127

(22) Filed: Jul. 12, 2005

(51) Int. Cl.
A61C 8/00 (2006.01)

(52) U.S. Cl. .......... 433/174; 433/172; 433/173

(58) Field of Classification Search ......... 433/172–176
See application file for complete search history.

(56) References Cited

U.S. PATENT DOCUMENTS

| | | | |
|---|---|---|---|
| 5,431,567 A | 7/1995 | Daftary | |
| 5,447,435 A | 9/1995 | Brodbeck | |
| 5,492,471 A | 2/1996 | Singer | |
| 5,685,714 A | 11/1997 | Beaty et al. | |
| 6,152,737 A | 11/2000 | Beaty et al. | |
| 6,619,958 B1 * | 9/2003 | Beaty et al. | 433/173 |
| 6,644,970 B1 * | 11/2003 | Lin | 433/173 |
| 6,663,388 B1 * | 12/2003 | Schar | 433/173 |
| 6,726,481 B1 * | 4/2004 | Zickmann et al. | 433/173 |
| 6,848,907 B1 | 2/2005 | Lee | |
| 2002/0018980 A1 * | 2/2002 | Yeung | 433/173 |
| 2003/0224329 A1 * | 12/2003 | Carlton | 433/173 |
| 2004/0053195 A1 * | 3/2004 | Blacklock | 433/173 |
| 2004/0076924 A1 * | 4/2004 | Kim | 433/173 |
| 2004/0191727 A1 * | 9/2004 | Shelemay et al. | 433/173 |
| 2005/0170311 A1 * | 8/2005 | Tardieu et al. | 433/76 |
| 2005/0175964 A1 * | 8/2005 | Shelemay et al. | 433/173 |
| 2005/0233281 A1 * | 10/2005 | Gittleman | 433/173 |

\* cited by examiner

*Primary Examiner*—Patricia Bianco
*Assistant Examiner*—Patrick J. Kilkenny
(74) *Attorney, Agent, or Firm*—Edwin Tarver; Patel & Alumit, P.C.

(57) ABSTRACT

A dental implant assembly comprising; a first part for fixing a tooth, a second part configured for receiving a threaded fastening means, said fastening means having a head portion and a threaded portion for fastening said first and second parts, a locking mechanism provided with both said first and second parts for locking rotational motion against each other on placing on top of one another, and, characterized in that; said first and second parts and head portion of the fastening means have predetermined profiles such that on screwing said fastening means into said second part a substantial part of the head portion descends into the second part and rests on the profiled sections of first and second parts making a complete contact, thereby, shielding threaded portion of the fastening means from masticating forces.

4 Claims, 13 Drawing Sheets

DENTAL IMPLANT SCREW AND POST SYSTEM

CROSS-REFERENCE TO RELATED APPPLICATION

None

FEDERALLY SPONSORED RESEARCH

None

SEQUENCE LISTING OR PROGRAM

None

STATEMENT REGARDING COPYRIGHTED MATERIAL

Portions of the disclosure of this patent document contain material that is subject to copyright protection. The copyright owner has no objection to the facsimile reproduction by anyone of the patent document or the patent disclosure as it appears in the Patent and Trademark Office file or records, but otherwise reserves all copyright rights whatsoever.

BACKGROUND

The present invention relates generally to prosthetics, and more specifically to dental implants, and, even more specifically to a dental implant, support post, and a screw having conical head, and, further more specifically to a support post having a hexagonal groove at the bottom and a hollow countersink to hold the aforesaid screw, and, an implant having a conical passage with the protruding hexagonal structure to partially accommodate the mentioned screw.

A dental implant is a device which is biocompatible and bio functional and is placed on or within the bone associated with the oral cavity to provide support for fixed or removable prosthetic teeth by means of screws.

frequently, the screws used in connection with the prosthesis may break on the inside of an implant, causing serious problems by damaging both the fixture and/or the prosthesis. A screw fracture is usually caused by abnormal stresses produced by the prosthesis. Another problem associated with dental implants is the loosening of screws that hold the implants in position.

The loosening action depends on stress forces typically caused by masticating forces (refer FIG. 1). However, depending on the frequency and/or the intensity of these forces, it is very likely to lose friction between the male and female threads that maintain the integrity of a coupling. What follows is imperceptible movement and micro-oscillations that subsequently can cause significant movement in the threading of the screw. This concept is common to virtually all fixation screws.

Considering a simple screw mechanism, on connecting the male and female counterparts without threading them completely, a small vertical movement can be noted. This is due to slight differences between the two threads and the space between them, called "tolerance" (refer FIG. 2).

Although engaging the thread completely causes the movement to cease because it enters a perfect engagement and fit (refer FIG. 3), mastication increases the deformation of the threads and causes the male part to rotate and unscrew over a period of time. This results in loosing of joint, and possibly a fracture.

U.S. Patent publication number U.S. Pat. No. 6,152,737 discusses a support post for use with a dental implant for supporting prosthesis. The problem with such post implants is that the screw, which connects the support post to the dental implant, is held at the shoulder region of the support post and hence the surface area in contact between the screw and the support post is substantially less resulting in a limited friction between the screw and the support post which intern results into loosening of the screw because of masticating forces. Further in this invention the screw head does not have any contact with the implant and therefore when a pressure is exerted on screw head, pressure is experienced by the thread and the bore area, which causes damage of the screw threads that may lead to fracture of screw and consequently the fracture of the implant itself. The constructional features of the invention are described in para [0031].

In another analogous art, U.S. Patent publication number U.S. Pat. No. 6,848,907 describes a screw for dental implant. This invention has similar limitations as discussed in the above-mentioned prior art.

In mentioned prior arts the torque and pressure exerted on the screw is unevenly distributed which causes breaking of the screw and damaging the implant; thus requiring surgical intervention. Therefore, the present scenario is punctuated by an emerging need for a dental implant that distributes the torque and the pressure evenly on the screw.

In view of the foregoing disadvantages inherent in the above-mentioned techniques, a general object of the present invention is to obviate above and other drawbacks associated with the prior art; to provide a system for an implant which can evenly bear the pressure exerted; to provide an improved assembly; to provide a screw with conical head which bears all the pressure thus preventing from the implant from fixture.

Other objects of the present invention are to provide a support post with an improved design which houses the screw conical head of the screw providing better holding and reducing the chances of under threading; to provide an improved implant with a conical passage to partially hold the conical head of the screw; and to hold the support post and implant firmly to prevent vertical circular motion of the support post over the implant. These and other objects of the present invention will become better understood with reference to the appended Summary, Description and Claims.

SUMMARY

This is a dental implant assembly comprising of a first part for fixing a tooth, a second part configured for receiving a threaded fastening means. The said fastening means, which can be a screw having a head portion and a threaded portion for fastening said first and second parts.

A locking mechanism provided with both said first and second parts by means of male-female locking and for locking rotational motion against each other they are placed on top of one another, and, characterized in that;

The said first and second parts and the head portion of the screw have a slanted profiles such that on screwing the screw into said second part a substantial part of the head portion of the screw descends into the second part and rests on the profiled sections of first and second parts making a complete contact, thereby, shielding threaded portion of the screw from masticating forces.

According to the second aspect of the invention A screw for dental implant assembly having at least a first and second part is provided which comprises, a slanted head portion, a threaded tail portion for fastening the dental implant assembly, such that a partial part of the head portion descends into both the first and second part of the dental implant assembly making a complete contact with said first and second parts of the dental implant assembly thereby, shielding threaded portion of the fastening means from masticating forces.

REFERENCE NUMERALS

1. Stress on Prosthesis
3. Prosthesis
5. Male Screw Thread
7. Female Screw Thread
9. Jaw
11. Female Side of the Screw
13. Male Side of the Screw
15. Tolerance
17. Threads in Perfect Contact
18. Support Post (Prior Art)
19. Screw
20. Hollow Passageway (Prior Art)
21. Conical Shaped Screw Head
22. Shoulder for Support
23. Screw Threads
24. Protruding Hexagonal Structure (Prior Art)
25. Support Post
26. Screw Thread Receiving Bore (Prior Art)
27. Hollow Passageway
28. (Prior Art)
29. Countersink/Conical Hollow Passageway
30. Screw Threads (Prior Art)
31. Grooved Hexagonal Structure
32. Implant (Prior Art)
33. Implant
35. Protruding Hexagonal Structure
37. Conical Passage
39. Screw Thread Receiving Bore

DETAILED DESCRIPTION

A further understanding of the present invention may be obtained with reference to the following description taken in conjunction with the accompanying drawings. However, the embodiments used for describing the invention are illustrative only and no way limiting scope of the invention. A person skilled in the art will appreciate that many more embodiments of the invention are possible without deviating from the basic concept of the invention any such embodiment will fall under the scope of the invention and is a subject matter of protection.

Figure 1:
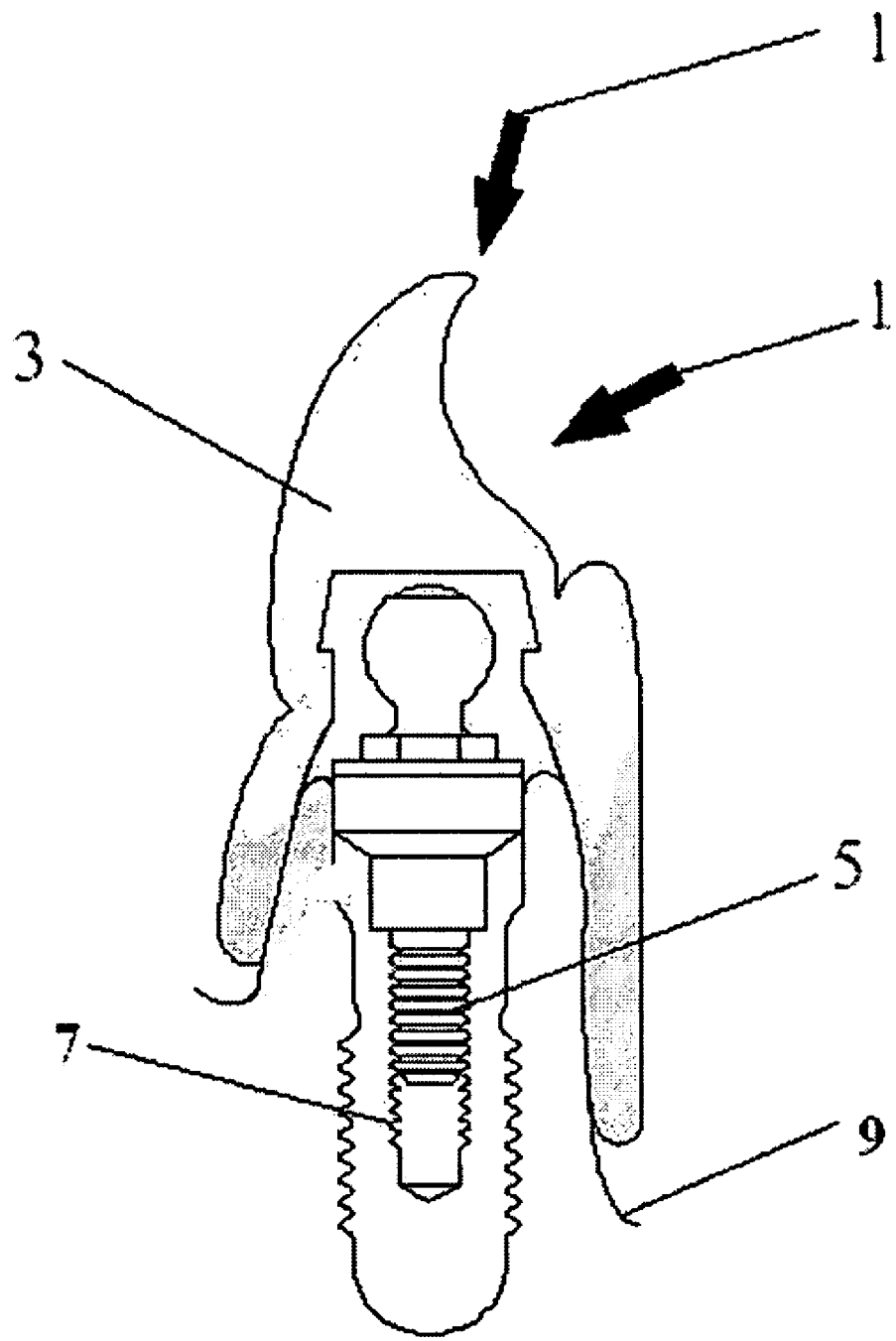
FIG. 1 is an illustration of the prosthesis experiencing stress due to masticatory forces.

FIG. 1 illustrates the abnormal forces/stresses induced on a typical prosthesis. Depending on the frequency and the intensity of different mastication forces 1 on the prosthesis 3, a loss of friction is caused between the male and female threads 5 and 7.

Figure 2:
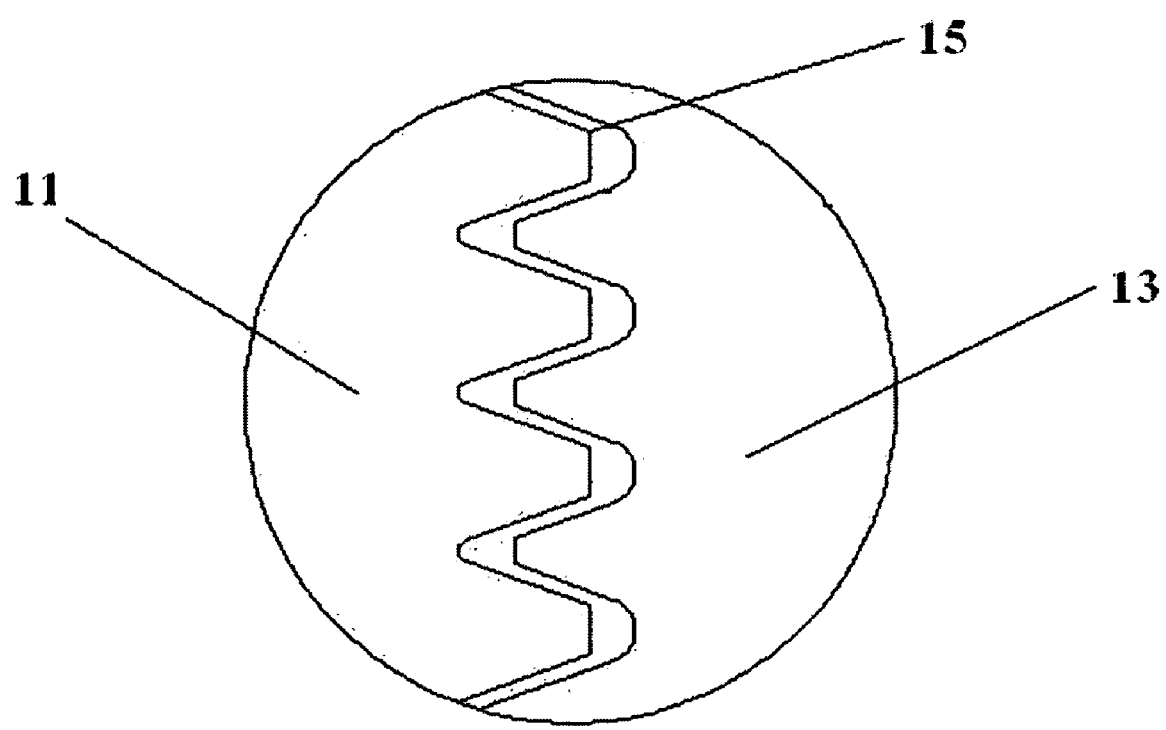
FIG. 2 is an illustration of the screw thread tolerance.

FIG. 2 is an illustration of the thread tolerance of the screw. The male screw thread 13 on the female screw thread bore 11 of the screw are connected without threading them completely, which leaves a small space between the threads of the male and female parts of the screw. This results in a small vertical movement due to the space between the two threads. This space between the threads, called the tolerance 15 of the screw can ultimately cause the screw to loosen.

Figure 3:
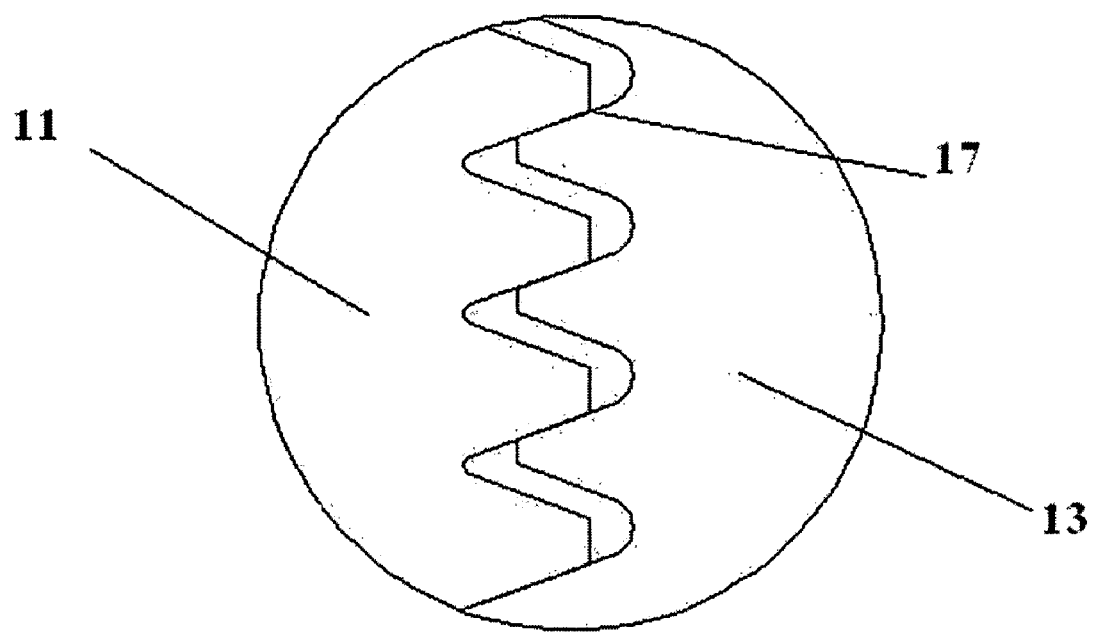
FIG. 3 is an illustration of a completely engaged screw thread which would eventually lead to screw fracture.

FIG. 3 is a comparative illustration of a pair of screw threads. These threads are in perfect alignment or engagement 17. This causes the movement of the threads 11, 13 to cease, and ultimately prevents the screw from loosening.

Figure 4:
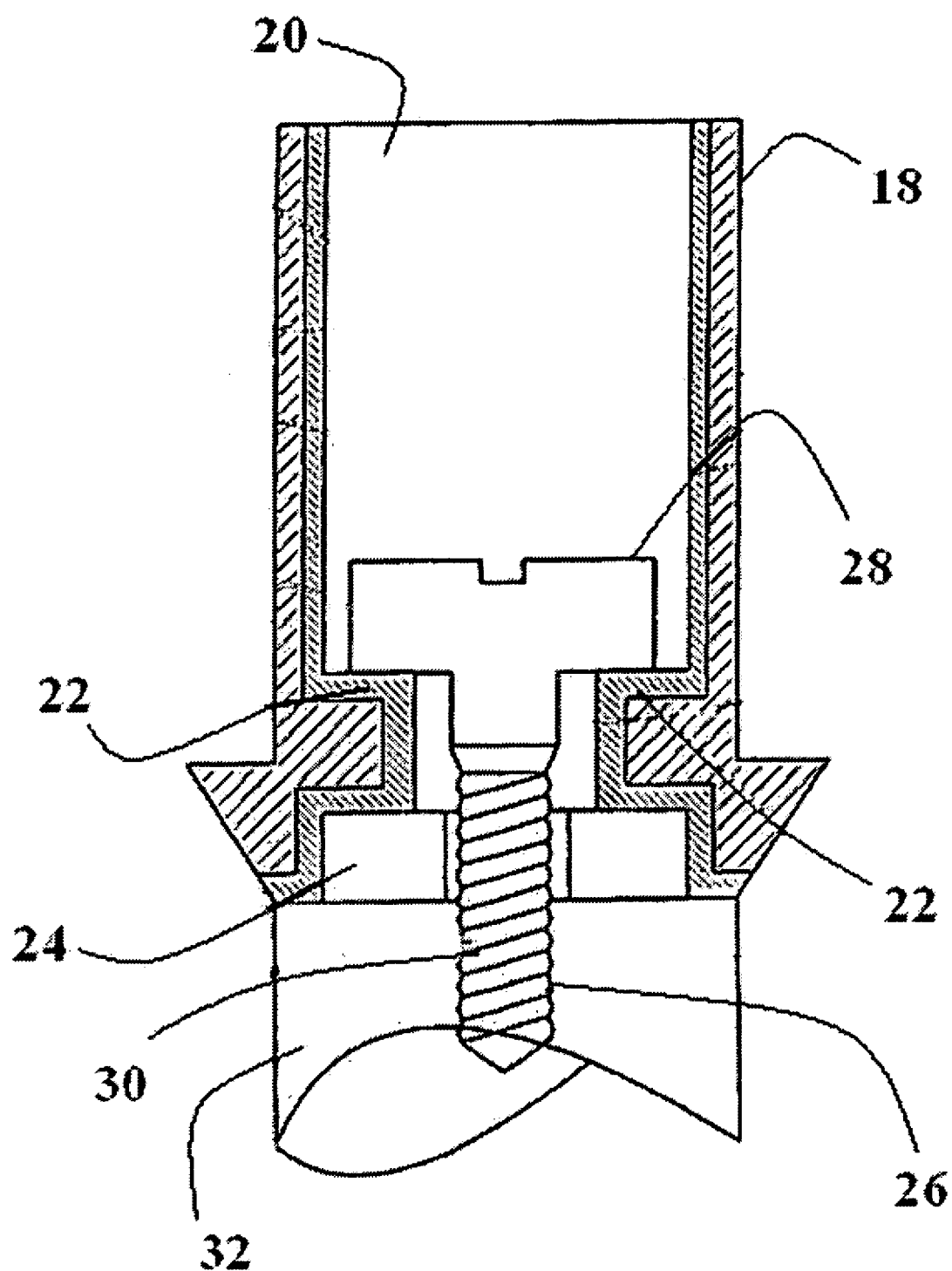
FIG. 4 is an illustration of the prior art which shows the support post in an assembled configuration with a dental implant.

FIG. 4 is an illustration of the prior art as described in U.S. Pat. No. 6,152,737, which depicts the support post 18 in an assembled configuration with the implant 32 and the support post 18 comprising of a hollow passageway 20 for the screw 28. The support post 18 and the implant 32 are coupled by means of connecting the grooved hexagonal shoulder 22 of the support post 18 to the protruding hexagonal structure 24 of the implant 32 and this couple is fastened by means of a screw 28. Limitations of this art are discussed in para [0007].

Figure 5:
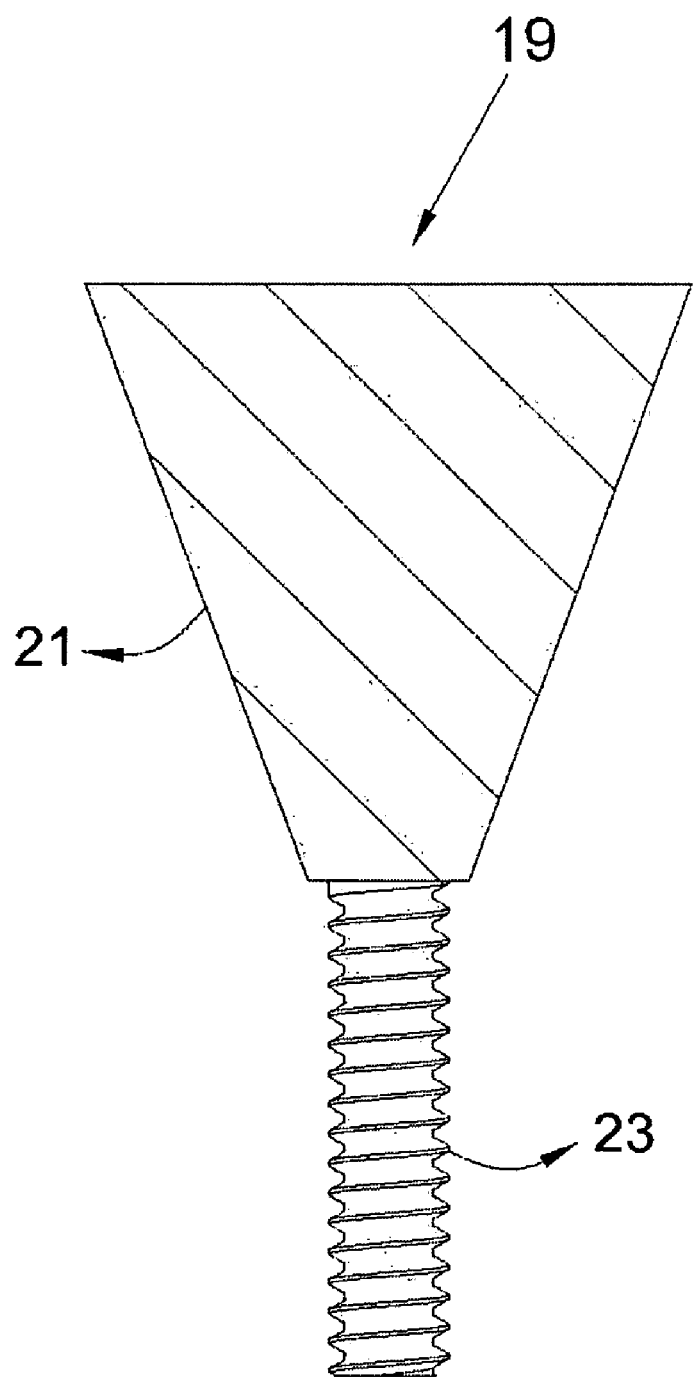
FIG. 5 is an illustration of a screw having a conical head.

FIG. 5 illustrates the side view of the conical screw 19 of the present invention. This screw is principally distinguished from a typical screw due to its conical head 21. A part of the conical shape goes into the conical passage 37 of the implant 33, providing added strength, and evenly distributing the force exerted at the time of mastication etc.

Figure 6:
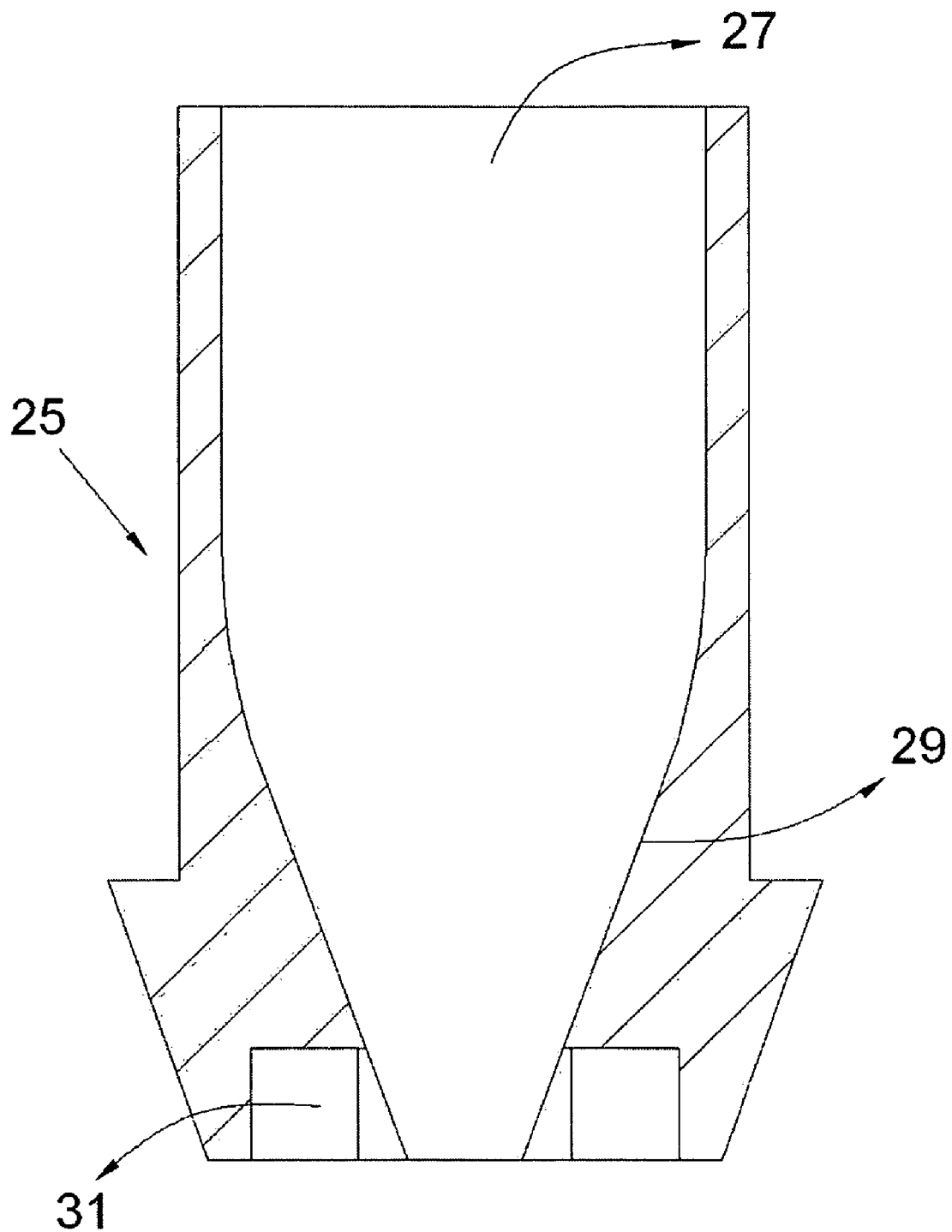
FIG. 6 is an illustration of the support post.

FIG. 6 is an illustration of the support post 25 of the implant 33 (refer FIG. 7) in accordance with the invention. It has a hollow passage way 27, a countersink/conical hollow passage way 29 for housing the conical screw head 19, and a hexagonal grooved structure 31 for locking rotational motion of the support post 25 and the implant 33 against each other. However, a person skilled in the art will appreciate that the rotational motion between two parts can be locked through many other mechanisms, including any male-female fixtures.

Figure 7:
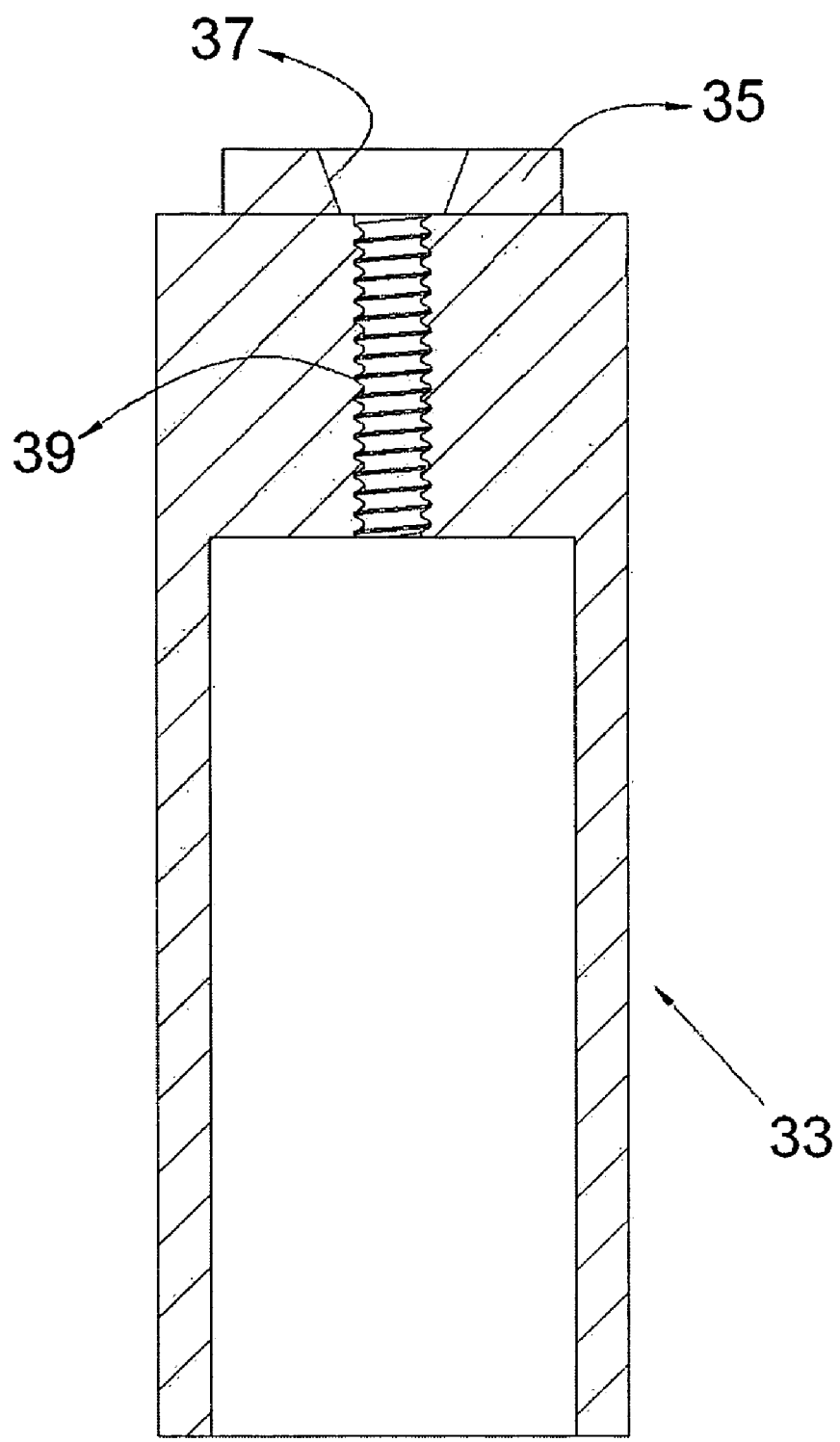
FIG. 7 is an illustration of the implant.

FIG. 7 is an illustration of the side view of the implant 33. It has a protruding hexagonal structure 35 for holding the support post 25 and a conical passage 37 is provided for partially holding the conical head 21 of the screw 19. Moreover, a screw thread receiving bore 39 for screwing the conically headed screw 19 is provided in it. When the support post 25 is placed on top of the implant 33. The protruding hexagon 35 of the implant 33 gets inserted into the grooved hexagon 31 of the support post 25 and therefore locks the rotational motion against implant 33 and support post 25. Further when the support post is placed on top of the implant, the countersink/conical hollow passageway 29 and conical passage 37 makes a regular conical shape for fixing the entire screw head in it, with the screw head making a perfect contact with the countersink/conical hollow passageway 29 and conical passage 37 thereby distributing any force exerted on the screw head 21 on the walls of the support post 22 and the implant therefore shielding the threaded part of the screw from stresses resulting into the increased life of the screw.

Figure 8:
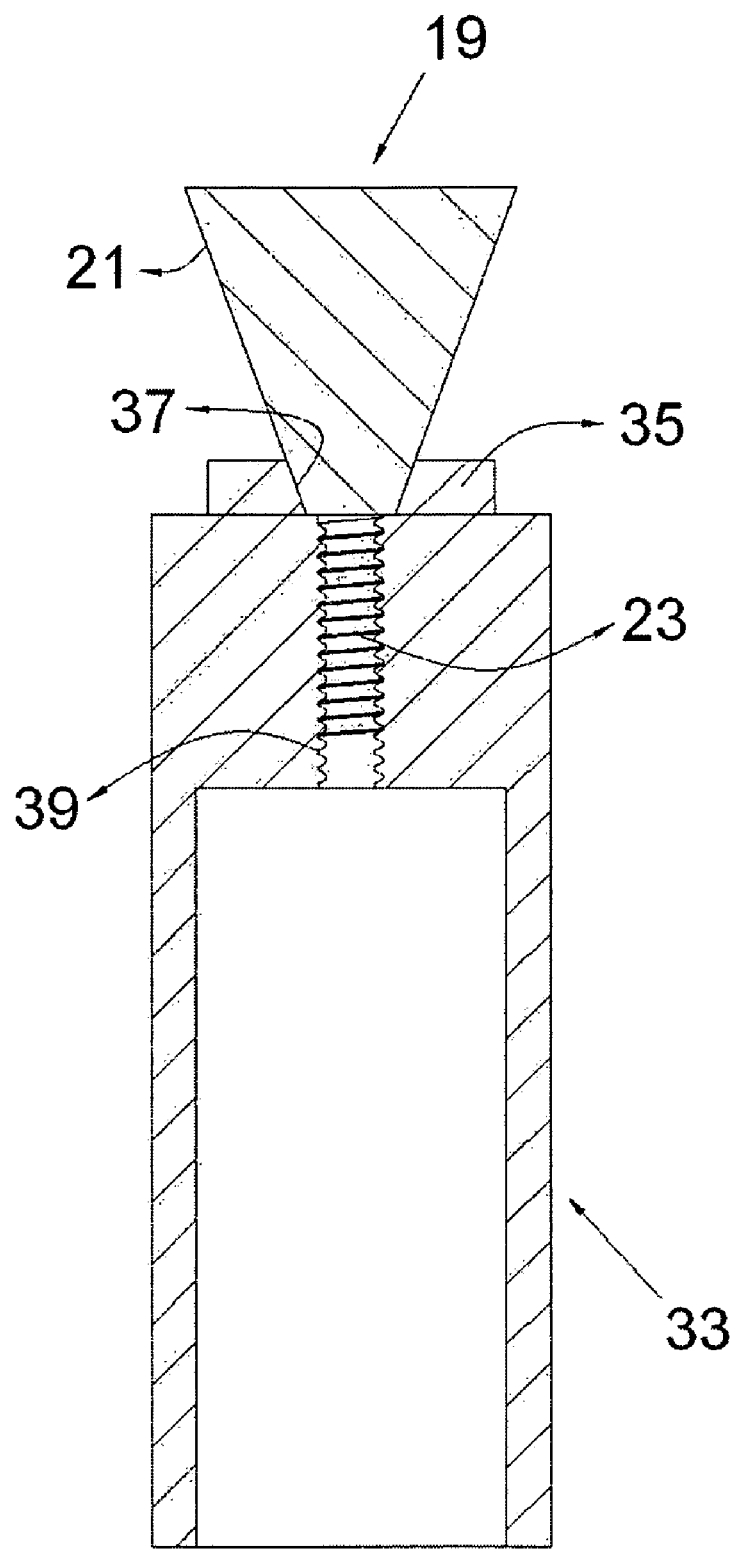
FIG. 8 is an illustration of the screw connected to the implant.

FIG. 8 is an illustration of the screw 19 connected to the implant 33 without connecting the support post 25. Here, the screw 19 is completely screwed into the implant 33 so that the lower part of the conical head 21 fits into the conical passage providing more strength to the complete assembly.

Figure 9:
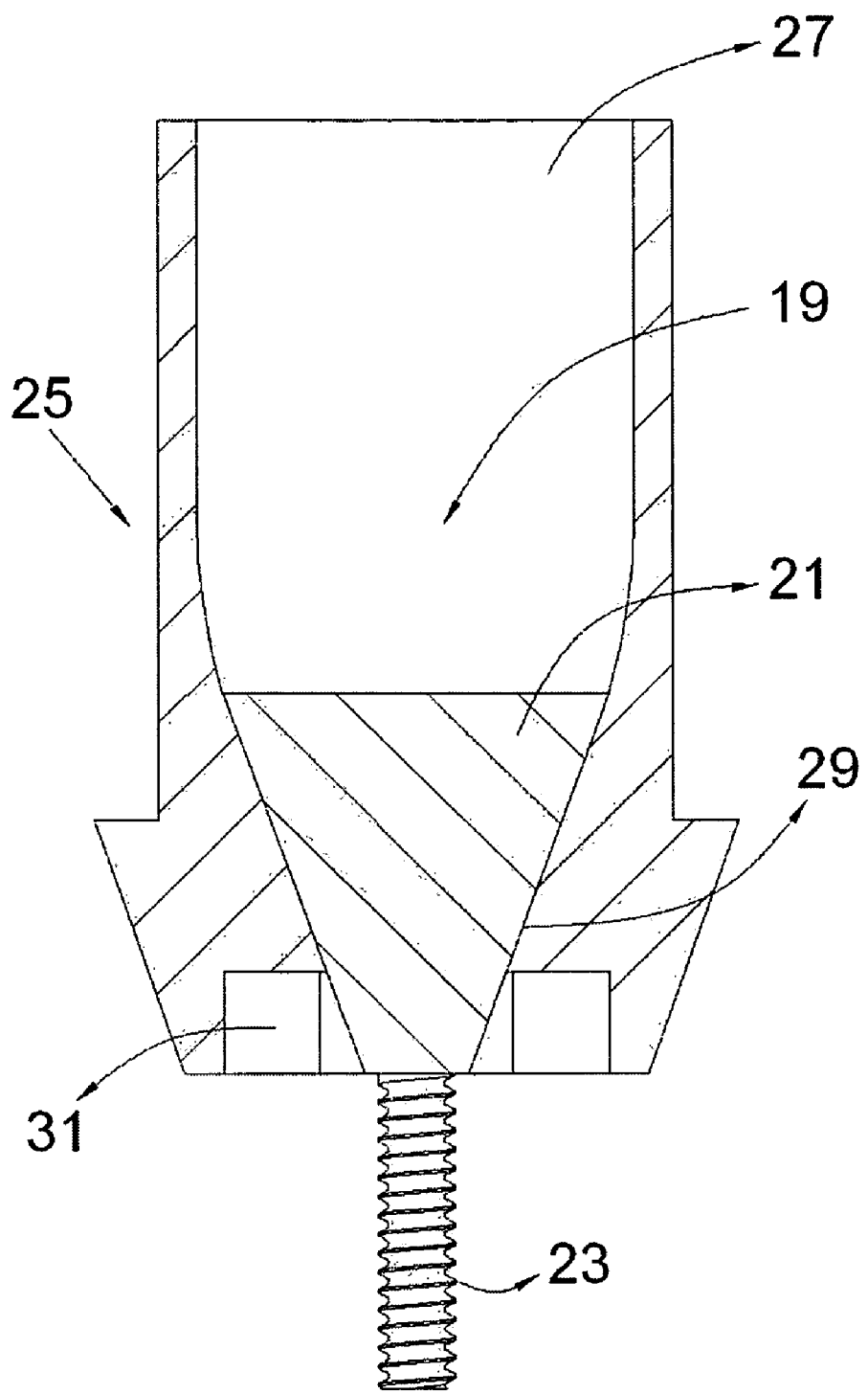
FIG. 9 is an illustration of the screw connected to the support post.

FIG. 9 is an illustration of the screw 19 connected to the support post 25, the conical head 21 of the screw 19 fits into the countersink/conical hollow passage way 29 of the support post 25 so that the complete assembly is perfectly coupled to bear the pressure without breaking.

Figure 10:
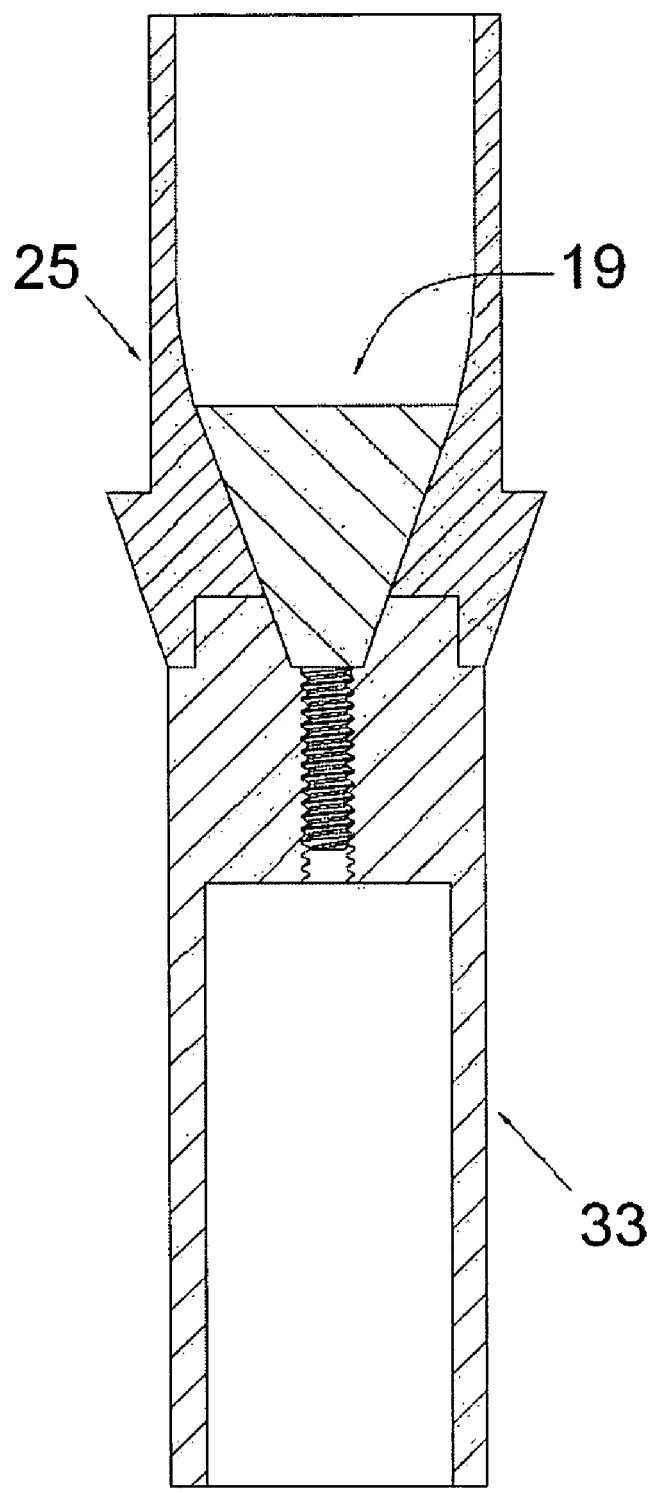
FIG. 10, FIG. 10A, FIG. 10B is an illustration of complete assembly.
Figure 10A:
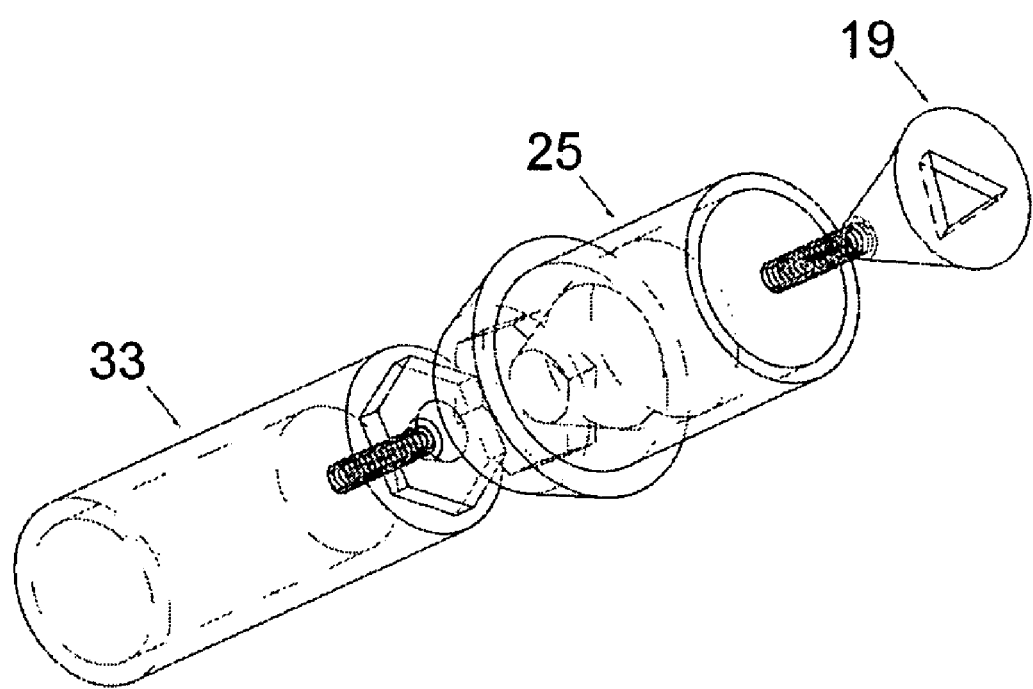
Figure 10B:
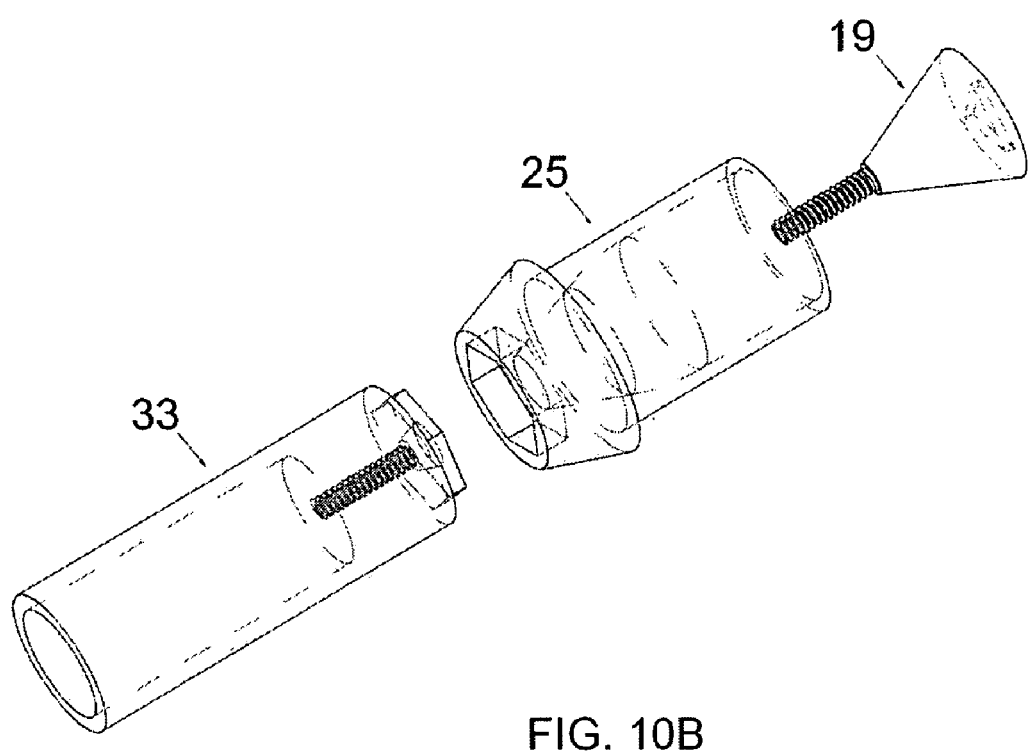

FIG. 10, FIG. 1A, FIG. 10B are different exploded views of the complete assembly of the dental implant. The material used in the assembly may be titanium or gold in different variations. Here the countersink 29 of support post 25 is shown holding the conical head 21 of the screw 19. Moreover, the protruding hexagonal structure 35 of the implant 33 is firmly fixing the support post 25 in its place through the hexagonal grooved structure 31.

At the same time, it must be noted that the grooved shape as well as the protruding shape are not limited to be hexagonal shape but it can be any polygon except a circle. The hexagonal shape may also be reversed, with the male portion of the hexagonal structure on the support post 25, and the female portion on the implant 33. To connect the support post 25 and implant 33, the screw 19 is screwed into the Screw thread receiving bore 39 of the implant 33.

Figure 11:
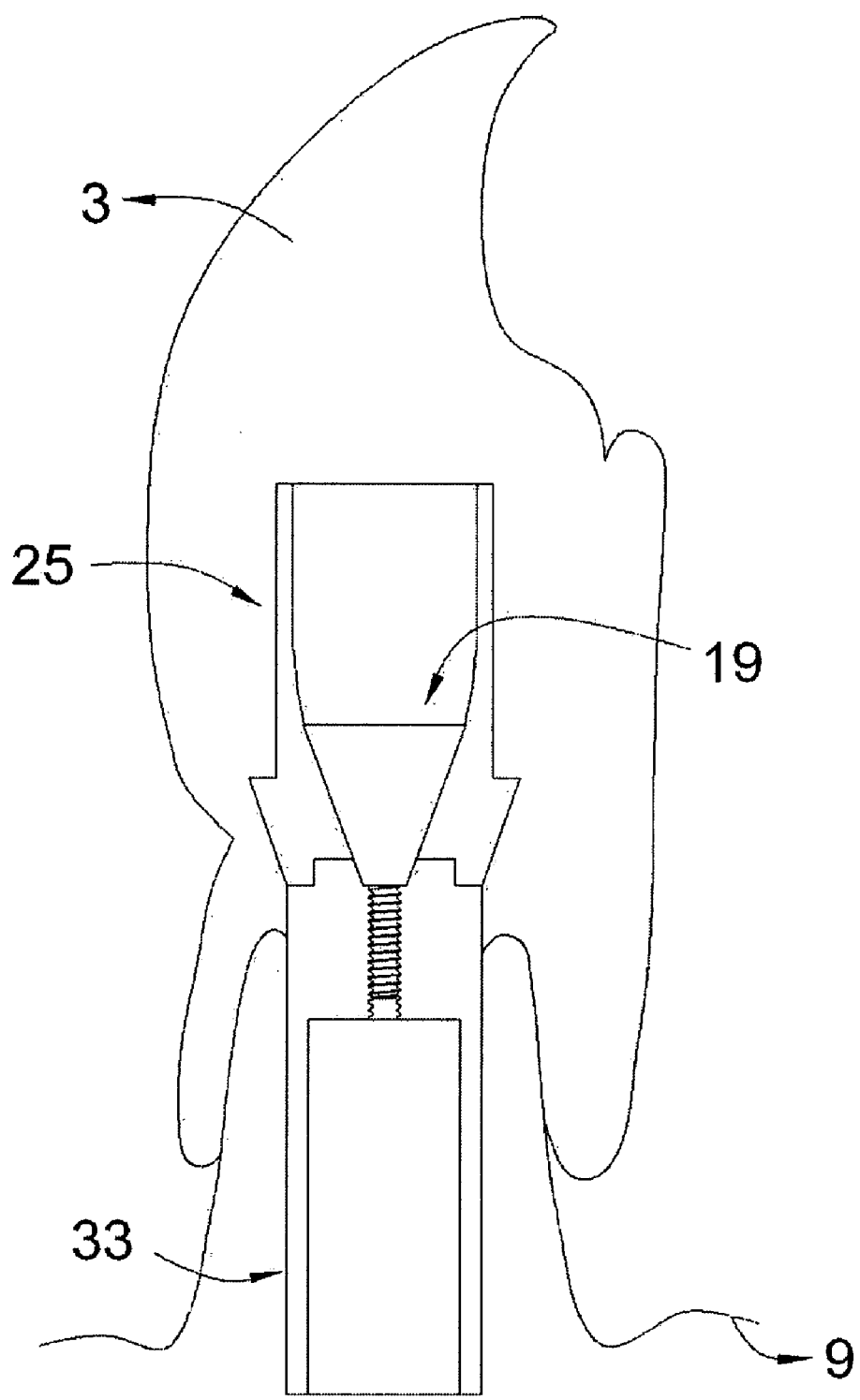
FIG. 11 is an illustration of the complete assembly in the prosthesis.

FIG. 11 is an illustration of the complete assembly in the prosthesis. The implant 33 is first fixed to the jaw 9, eventually adhering through ossiointegration or functional ankylosis. Then the implant 33 is coupled with the support post 25 by means of the screw 19 and on the top of the assembly is the prosthesis 3, which may be held in place with screws, cement, or by other means.

What is claimed is:

1. A dental implant assembly comprising;
    a first part for fixing to a tooth implant comprising a cylindrical member with an open top end of a first inner diameter, an open bottom end of a lesser inner diameter, and a uniformly inwardly slanting diameter depending downward along the interior of the cylinder, outlining a conical shape;
    a second part for fixing to a jaw comprising a cylindrical member with a top surface comprising an inwardly slanting diameter depending downward from the surface, outlining a conical shape, and terminating in a threaded bore;
    a male to female locking mechanism on the bottom surface of the first part and top surface of the second part that prevents rotational motion; and a fastening means having a top head portion and a bottom threaded portion for fastening the first and second parts together; wherein
    the fastening means' top head portion comprises a top surface for engaging a tightening tool, and a slanting side surface, complimentary to the slanted interior profiles of the first and second parts, rendering the top head portion of the fastening means three dimensionally conical; and such that upon fixing the fastening means into the connected first and second parts, the entire conical side surface of the fastening means makes uniform contact along the interior of the first and second parts, and a substantial amount of the head portion descends into the interior slanted dimension of the second part, thereby distributing pressure evenly across both parts and the fastening means.

2. The dental implant assembly of claim 1, wherein the fastening means is a screw with head portion with uniform slanting sides, and a threaded portion attached to bottom of the head portion, and the locking mechanism is any locking mechanism that comprises a male-female structure to prevent rotational motion.

3. The dental implant assembly of claim 2, wherein a bottom portion of the first part and a top portion of the second part accommodate the slanted profile of the head portion of the fastening means across their interior surfaces, the slanted profiles on the first and second parts are sloped towards their centers and are adapted to achieve a gapless interface with the conical-shaped head portion of the screw.

4. A dental implant assembly comprising;
    a first part for fixing a tooth, a bottom portion of the first part including a first conical passageway on its interior surface;
    a second part for fixing to a jaw, a top portion of the second part including a second conical passageway on its interior surface;
    a locking mechanism on both the first and second parts for preventing rotational motion between the first and second parts when they are joined together;
    a fastening means having a conical-shaped head portion and a threaded portion attached to bottom of the conical-shaped head portion for fastening the first and second parts, the second part configured for receiving the threaded portion of the fastening means; wherein
    the conical-shaped head portion abuts the conical passageways of the first and second parts making a complete contact, evenly distributing pressure forces over the slanted profiles to preventing the fastening means from loosening or breaking.

* * * * *